United States Patent
Johnson, Jr. et al.

(10) Patent No.: US 12,405,260 B2
(45) Date of Patent: *Sep. 2, 2025

(54) MULTIPLEXED DETECTION OF TOXINS USING GRAPHENE-BASED APTASENSORS

(71) Applicant: The Trustees of the University of Pennsylvania, Philadelphia, PA (US)

(72) Inventors: Alan T. Johnson, Jr., Philadelphia, PA (US); Jinglei Ping, Gaithersburg, MD (US); Steven Vitale, Collingswood, NJ (US); Chengyu Wen, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,369

(22) Filed: Nov. 8, 2023

(65) Prior Publication Data

US 2024/0319160 A1    Sep. 26, 2024

Related U.S. Application Data

(63) Continuation of application No. 16/299,615, filed on Mar. 12, 2019, now Pat. No. 11,846,622.
(Continued)

(51) Int. Cl.
*G01N 33/18* (2006.01)
*G01N 27/04* (2006.01)

(52) U.S. Cl.
CPC ......... *G01N 33/1813* (2013.01); *G01N 27/04* (2013.01); *G01N 33/1826* (2013.01); *G01N 2410/00* (2013.01)

(58) Field of Classification Search
CPC ............... G01N 33/1813; G01N 27/04; G01N 33/1826; G01N 2410/00; G01N 27/4145
See application file for complete search history.

(56) References Cited

U.S. PATENT DOCUMENTS

| | | |
|---|---|---|
| 2010/0112546 A1 | 5/2010 | Lieber et al. |
| 2010/0268479 A1 | 10/2010 | Potyrailo et al. |

(Continued)

FOREIGN PATENT DOCUMENTS

| | | |
|---|---|---|
| KR | 10-2014-0014774 A | 2/2014 |
| WO | 2006/024023 A2 | 3/2006 |

OTHER PUBLICATIONS

Benvidi et al. "Comparison of impedimetric detection of DNA hybridization on the various biosensors based on modified glassy carbon electrodes with PANHS and nanomaterials of RGO and MWCNTs"—Talanta, vol. 147, Jan. 15, 2016, pp. 621-627. (Year: 2016).*

(Continued)

*Primary Examiner* — Benjamin R Schmitt
(74) *Attorney, Agent, or Firm* — BakerHostetler

(57) ABSTRACT

Provided is a sensor device, comprising: a portion of graphene and/or graphene oxide in electronic communication with a gold source electrode, a drain electrode, a gate electrode, or any combination thereof; and an aptamer in electrical communication with the portion of graphene and/or graphene oxide, the portion of graphene and/or graphene oxide connected to said aptamer via at least one linker that comprises 4-carboxybenzenediazonium tetrafluoroborate.

3 Claims, 17 Drawing Sheets

Specification includes a Sequence Listing.

Related U.S. Application Data

(60) Provisional application No. 62/641,476, filed on Mar. 12, 2018.

(56) References Cited

U.S. PATENT DOCUMENTS

| | | |
|---|---|---|
| 2011/0217763 A1 | 9/2011 | Rasooly et al. |
| 2017/0181669 A1 | 6/2017 | Lin et al. |
| 2017/0350856 A1* | 12/2017 | Kobayashi ......... G01N 27/4145 |

OTHER PUBLICATIONS

Wu et al. "Doping effects of surface functionalization on graphene with aromatic molecule and organic solvents"—Applied Surface Science, vol. 425, Dec. 15, 2017, pp. 713-721. (Year: 2017).*
An et al., "High-performance flexible graphene aptasensor for mercury detection in mussels", ACS Nano, 2013, vol. 7, No. 12, p. 10563-10571.
Anonymous, "Bisphenol A in Drinking Water", http://www.health.state.mn.us/divs/eh/risk/guidance/gw/bpainfosheet.pdf; Minnesota Department of Health: 2014.
Anonymous, "Environmental Protection Agency Safe Drinking Water Act Standards: Microbiological, Radiological, and Inorganic Contaminants", https://www.health.state.mn.us/communities/environment/water/factsheet/sdwa.html Department of Health: 2014.
Balandin, "Low-frequency 1/f noise in graphene devices", Nature Nanotechnology, 2013, vol. 8, pp. 549-555.
Ballesteros-Gomez et al., "Analytical methods for the determination of bisphenol A in food", Journal of Chromatography A, 2009, vol. 1216, pp. 449-469.
Chen et al., "Charge-impurity scattering in graphene", Nature Physics, 2008, vol. 4, pp. 377-381.
Fukata et al., "Comparison of Elisa- and LC-MS-Based Methodologies for the Exposure Assessment of Bisphenol A", Toxicology Mechanisms and Methods, 2006, vol. 16, pp. 427-430.
Gumpu et al., "A review on detection of heavy metal ions in water—An electrochemical approach", Sensors and Actuators B: Chemical, 2015, vol. 213, pp. 515-533.
Huang et al., "Colorimetric Detection of Heavy Metal Ions Using Label-Free Gold Nanoparticles and Alkanethiols", The Journal of Physical Chemistry C, 2010, vol. 114, No. 39, pp. 16329-16334.
Jo et al., "Development of Single-Stranded DNA Aptamers for Specific Bisphenol A Detection", Oligonucleotides 2011, vol. 21, pp. 85-91.
Keefe et al., "Aptamers as therapeuticc", Nature Reviews 2010, vol. 9, pp. 537-550.
Lerner et al., "Large scale commercial fabrication of high quality graphene-based assays for biomolecule detection", Sensors and Actuators B: Chemical, 2017, vol. 239, pp. 1261-1267.
Li et al., "Fully integrated graphene electronic biosensor for label-free detection of lead (II) ion based on G-quadruplex structure-switching", Biosensors and Bioelectronics, 2016, vol. 89, pp. 758-763.
Ohno et al., "Label-Free Biosensors Based on Aptamer-Modified Graphene Field-Effect Transistors", Journal of American Chemical Society, 2010, vol. 132, No. 51, pp. 18012-18013.
Ping et al., "Quantifying the effect of ionic screening with protein-decorated graphene transistors", Biosensors and Bioelectronics, 2017, vol. 89, pp. 689-692.
Ping et al., "Scalable Production of High-Sensitivity, LabelFree DNA Biosensors Based on Back-Gated Graphene Field Effect Transistors", ACS Nano., 2016, vol. 10, No. 9, pp. 8700-8704.
Qu et al., "Rapid and Label-Free Strategy to Isolate Aptamers for Metal Ions", ACS Nano., 2016, vol. 10, pp. 7558-7565.
Stuart et al., "Analyses of phenolic endocrine disrupting chemicals in marine samples by both gas and liquid chromatography-mass spectrometry", Journal of Chromatography A, 2005, vol. 1079, pp. 136-145.
Vishnubhotla et al., "Scalable graphene aptasensors for drug quantification", AIP Advances, 2017, pp. 1-7.
Weiss, "The Hill equation revisited: uses and misuses", Faseb J., 1997, vol. 11, No. 11, pp. 835-841.
Wiedman et al., "An Aptamer-Based Biosensor for the Azole Class of Antifungal Drugs", mSphere 2017, vol. 2, Issue 4, e00274-17, pp. 1-10.

* cited by examiner

SEQUENCE LISTING

```
Sequence total quantity: 3
SEQ ID NO: 1           moltype = DNA  length = 63
FEATURE                Location/Qualifiers
source                 1..63
                       mol_type = other DNA
                       organism = synthetic construct
SEQUENCE: 1
ccggtgggtg gtcaggtggg atagcgttcc gcgtatggcc cagcgcatca cgggttcgca    60
cca                                                                  63

SEQ ID NO: 2           moltype = DNA  length = 60
FEATURE                Location/Qualifiers
source                 1..60
                       mol_type = other DNA
                       organism = synthetic construct
SEQUENCE: 2
cgcagcgcgc ccctgagtac tgtccgccca acggtgtgac ggccctgcga tcaacgattg    60

SEQ ID NO: 3           moltype = DNA  length = 51
FEATURE                Location/Qualifiers
source                 1..51
                       mol_type = other DNA
                       organism = synthetic construct
SEQUENCE: 3
tccaagctct tttctgcagc tattcttgtt tcgaaacttg ctaagctgcg t             51
```

MULTIPLEXED DETECTION OF TOXINS USING GRAPHENE-BASED APTASENSORS

CROSS-REFERENCE TO RELATED APPLICATION

This application is a continuation of now-allowed U.S. patent application Ser. No. 16/299,615, "Multiplexed Detection Of Toxins Using Graphene-Based Aptasensors" (filed Mar. 12, 2019); which claims priority to and the benefit of U.S. Provisional Application No. 62/641,476, "Multiplexed Detection Of Toxins Using Graphene-Based Aptasensors" (filed Mar. 12, 2018). All foregoing applications are incorporated herein by reference in their entireties for any and all purposes.

GOVERNMENT RIGHTS

This invention was made with Government support under grant number 1P30 ES013508 awarded by the National Institute of Environmental Health Sciences, National Institutes of Health. The government has certain rights in the invention.

SEQUENCE LISTING

This application contains a Sequence Listing which is being submitted herewith electronically in XML format and is hereby incorporated by reference in its entirety. Said XML copy, created on May 21, 2024, modified on May 29, 2024, is named 104377000318(18-8470)_Sequencelisting.xml and is 3,935 bytes in size.

TECHNICAL FIELD

The present disclosure relates to the fields of semiconductor devices, pathogen detection, and aptamers.

BACKGROUND

Toxins in environmental water bodies pose significant threats to the health of people exposed to them. There is long-felt need to simultaneously monitor organic and inorganic toxins, such as bisphenol A (BPA) and mercury ions Hg(II), that can coexist in the field, with high sensitivity and selectivity.

Typically, organic toxins are be detected by analytical chemistry methods such as liquid chromatography or immune-enzyme assays; heavy metal ions can be detected by electrochemical or colorimetric techniques. These conventional approaches, though very effective for lab-based quantitative analysis, lack efficiency in terms of cost, size, time, and power-consumption, making them unsuitable for use in the field or real-time monitoring. Moreover, those different techniques are based on different detection mechanisms and can be challenging to integrate together. Accordingly, there is a long-felt need in the art for improved analyte detection systems.

SUMMARY

In meeting the described long-felt needs, the present disclosure first provides sensor devices, comprising: a portion of graphene and/or graphene oxide; and an aptamer in electrical communication with the portion of graphene and/or graphene oxide.

Also provided are methods, comprising: contacting a sensor device according to the present disclosure with a sample; and measuring an electrical signal of the sensor device related to an interaction between the aptamer and the sample.

Further disclosed are methods, comprising: contacting a sample to an aptamer in electronic communication with a portion of graphene and/or graphene oxide; and measuring an electrical signal of the sensor device related to an interaction between the aptamer and the sample.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

DETAILED DESCRIPTION OF ILLUSTRATIVE EMBODIMENTS

Figure 1A:
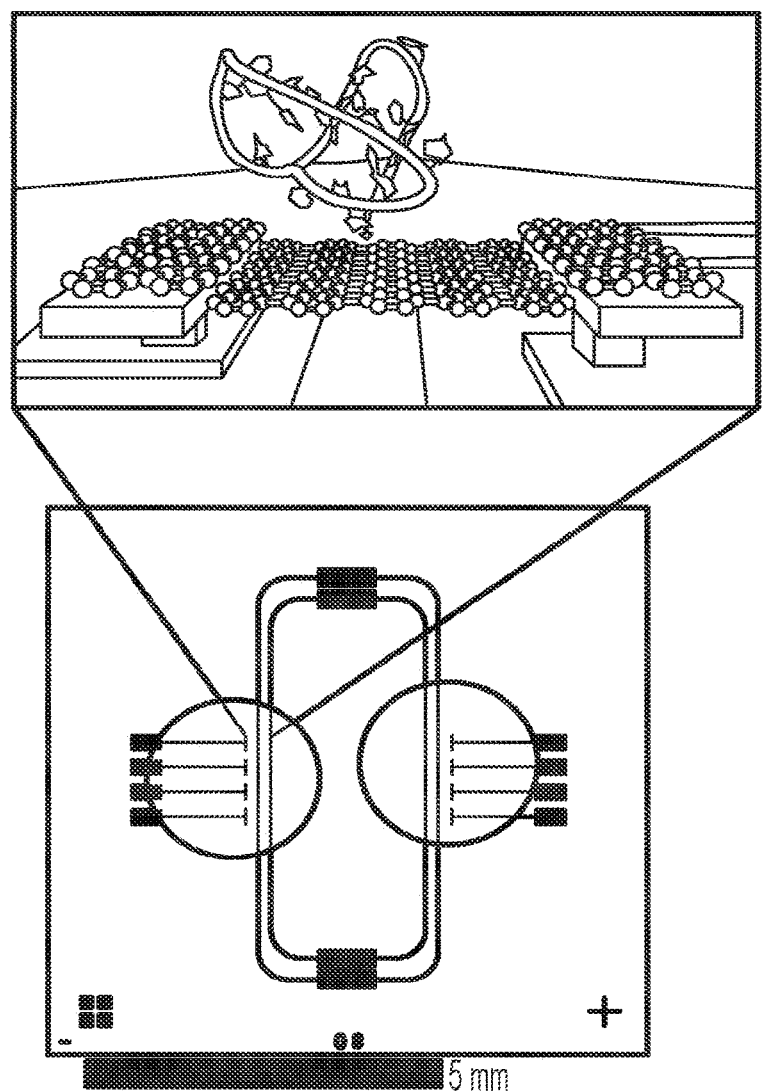
FIG. 1A provides an array consisting of eight graphene-aptamer field-effect transistors with a schematic showing a single functionalized transistor. Different parts of the array can be functionalized by different type of aptamers (e.g., left hand aptamer solution can differ from the right hand aptamer solution)

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable, and it should be understood that steps may be performed in any order. Any documents cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. In addition, the term "comprising" should be understood as having its standard, open-ended meaning, but also as encompassing "consisting" as well. For example, a device that comprises Part A and Part B may include parts in addition to Part A and Part B, but may also be formed only from Part A and Part B.

The multiplexed aptasensor system disclosed herein represents a successful effort to integrate graphene-based bioelectronics with conventional electronics. The disclosed systems will be useful in, e.g., environmental monitoring and toxicology, and the technology in general is also useful in graphene-enabled biosensing applications in point-of-care diagnostics and healthcare.

Transistors based on graphene-aptamer hybrids can be translated into all-electronic systems for multiplexed toxin detection. As a single-atom thick layer of $sp^2$ carbon atoms arranging in honeycomb lattice, graphene is an ideal signal transduction material due to its high susceptibility to surrounding electrostatic variation, ultra-low electrical noise, and compatibility to conventional electronics; DNA-based aptamers with indefinite shelf life, high stability, and simple and controllable production, are particularly suitable to be used as the chemical recognition elements in biosensors. In some embodiments, the aptamer is, e.g., a DNA or RNA or an XNA aptamer. An aptamer can also be a peptide aptamer.

Provided here is, e.g., a graphene aptasensor-based multiplexed system capable of monitoring toxins (e.g., organic/inorganic toxins in tap water) in real time. Also provided here is a scalable fabrication protocol to produce aptasensing arrays based on graphene field-effect transistors (gFETs), with a novel configuration that allows the driving electronics to be programmed to back-gate each transistors individually.

Illustrative Disclosure

The charge density for gFETs in an array fabricated by state-of-the-art protocol can vary, e.g., by $\pm 2.9 \times 10^{11}$ cm$^{-2}$ from one device to another device. This strategy enables (1) calibration of the back-gate voltage of all transistors at their working and analytical range and (2) maximization of their sensitivity. An array can be driven by handheld electronics that can be programmed to interrogate transduction signals and transmit data wirelessly with low power-consumption.

In illustrative embodiments, a system according to the present disclosure was used to detect two toxins that exist universally in drinking water and can lead to severe health issues, BPA and Hg(II), with detection limit orders of magnitude smaller than guidelines suggested by authorized healthy departments/organizations. The disclosed systems can, of course, be used for real-time quality monitoring of real-world water bodies as well as other applications, e.g., applications in environmental toxicology.

Figure 1B:
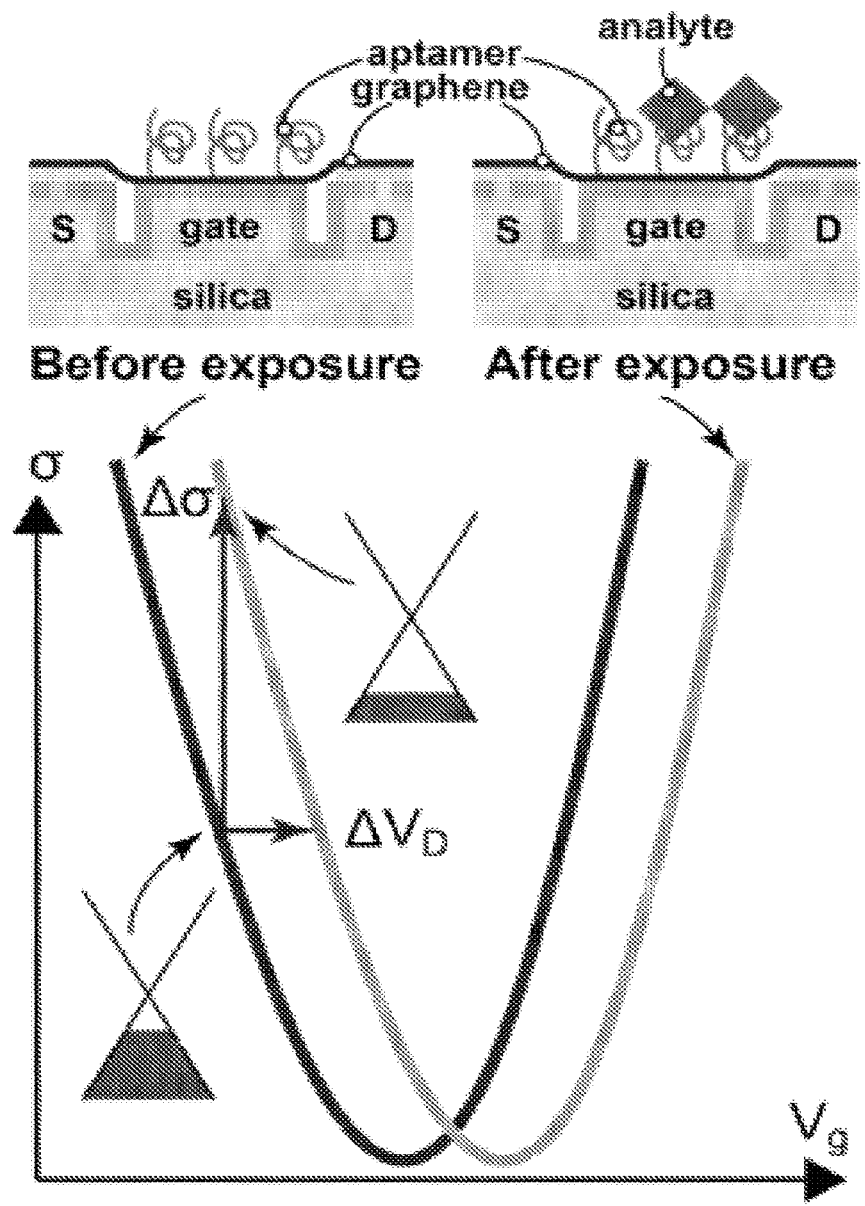
FIG. 1B provides a device configuration and sensing mechanism of gFET-based aptasensors of the array.

Provided here is a scalable approach to produce sensing arrays using photolithography techniques and chemical functionalization protocols. As shown in FIG. 1a and FIG. 1b, gFETs were built on a 1 mm thick fused silica; gold source (S), drain (D), and gate leads were passivated by 50 nm thick $HfO_2$ except at areas that contact to graphene channel or be used for wire-bonding. The $HfO_2$ with high relative dielectric constant (~30) also serves as the dielectric layer that allows to tune the carrier density of graphene channel over a broad range (0 to $4.8 \times 10^{14}$ cm$^{-2}$).

Aptamer biomolecules against BPA or Hg(II) were immobilized on the graphene channel through 1-pyrenebutyric acid N-hyroxysuccinimide ester (PBASE), a bifunctional linker, with high coverage efficiency (>1000 molecules per $\mu m^2$). High coverage efficiency is useful—but not necessarily required—for production of aptasensors with high sensitivity. Regions functionalized by different types of aptamers can be gated separately to maximize the sensitivity. The functionalized array was fixed on a chip carrier, the pads were wire bonded, and the leads were encapsulated with epoxy.

When the array was exposed to the solution comprising the target(s), the analyte-aptamer binding induced variation of graphene charge carrier density by chemical gating effect. As a result, the charge neutral point of graphene, or the voltage that corresponding to the minimal conductance in the V-shape graphene conductance-back gate voltage characteristics $\sigma$-$V_g$, will be shifted by $\Delta V_D$ (FIG. 1b), which represents the variation in carrier density through $\Delta n = c_{ox} \Delta V_D$, where $c_{ox}$ ~5.3 mF m$^{-2}$ is the specific capacitance for the $HfO_2$ dielectric layer.

Because $\Delta n$ is proportional to the total amount of target binding to the aptamer-graphene hybrid, $\Delta V_D$ can be well described by the Hill-Langmuir equation, $$\Delta V_D = A_V \frac{(c/K_d)^a}{1 + (c/K_d)^a},$$

with $A_V$ the magnitude of the sensor response in term of $\Delta V_D$, $K_d$ the dissociation constant for the analyte-aptamer binding, and a the Hill coefficient.

According to the Drude model, the graphene conductance σ is equal to eμn, where μ, the field-effect mobility of the graphene, is identical to the slope of the σ-$V_g$ characteristic beyond the charge neutral point. Because μ does not change much (<5%) as analytes binds to functionalized gFETs, one may fix $V_g$ at an "optimized" value with maximized transconductance (dσ/d$V_g$) beyond the charge neutral point for the real-time measurement of the aptasensors. This "tuning" step allows all the gFETs to be operated at their working range of charge carrier density, enabling programmable calibration of carbon-based transistor array by conventional electronics. Furthermore, this strategy ensures that the BPA aptasensor delivers the maximized sensitivity and the conductivity variation, Δσ, is proportional to $\Delta V_D$. Thus at the optimized point of $V_g$:

$$\Delta\sigma = A_\sigma \frac{(c/K_d)^n}{1+(c/K_d)^n} \quad (1)$$

where $A_\sigma$ the magnitude of the sensor response in terms of conductance variation.

Figure 2A:
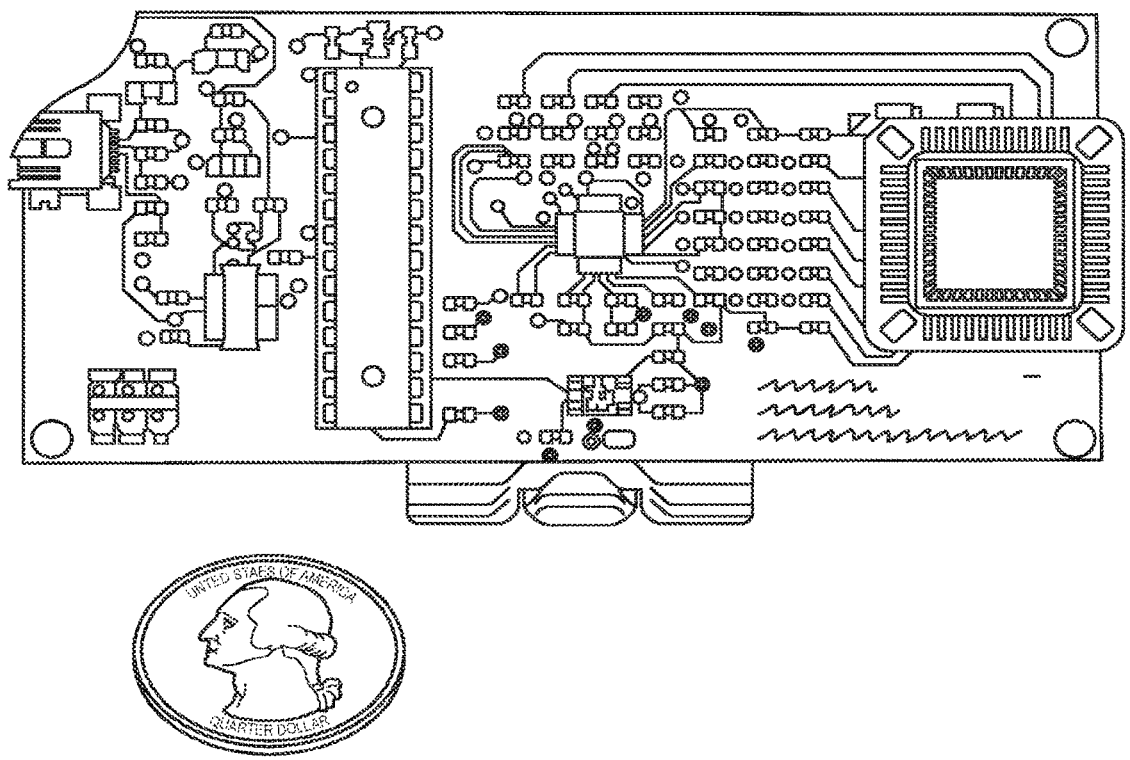
FIG. 2A provides an exemplary miniaturized electronics arrangement that drives the array of aptasensors based on graphene field-effect transistors.

To fill the need for a lab/benchtop-based and self-sufficient system, provided here are programmable chip-based electronics on a credit card sized electronic circuit board (ECB, FIG. 2a) that can be integrated with the array of gFETs and allows automatic gFET testing, data acquisition, and wireless signal transceiving.

Figure 2B:
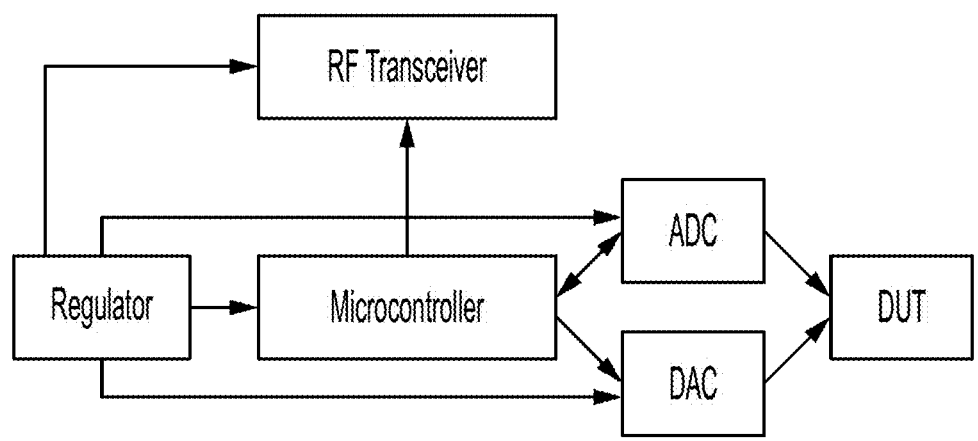
FIG. 2B provides exemplary circuitry for the electronics.

In one embodiment, the circuitry (FIG. 2b) contains a voltage regulator that maintains the supply level (5 V) for an AVR RISC-based micro-controller unit (MCU) that controls an analog-to-digital converter (ADC), a digital-to-analog converter (DAC), and also a cm-size external wireless radio-frequency (RF) transceiver through a serial peripheral interface (SPI) bus. The ADC featured 24-bit resolution (nV detection limit), 12-channels with data rates up to 4k sampling per second, and low power consumption (~300 μW at 100 Hz sampling rate).

For the electronics interface, the source-drain current of the gFET sensor device under test (DUT) was provided by a low-noise current source (2 μA-2 mA) integrated in the ADC; the gate voltage was provided by the DAC controlled by the MCU. Input and output signals for the DUT are stabilized by a RC low-pass filtering network to reduce common noise and differential noise without diminishing the susceptibility of the signal interrogation at operating frequency >4 KHz.

Figure 2C:
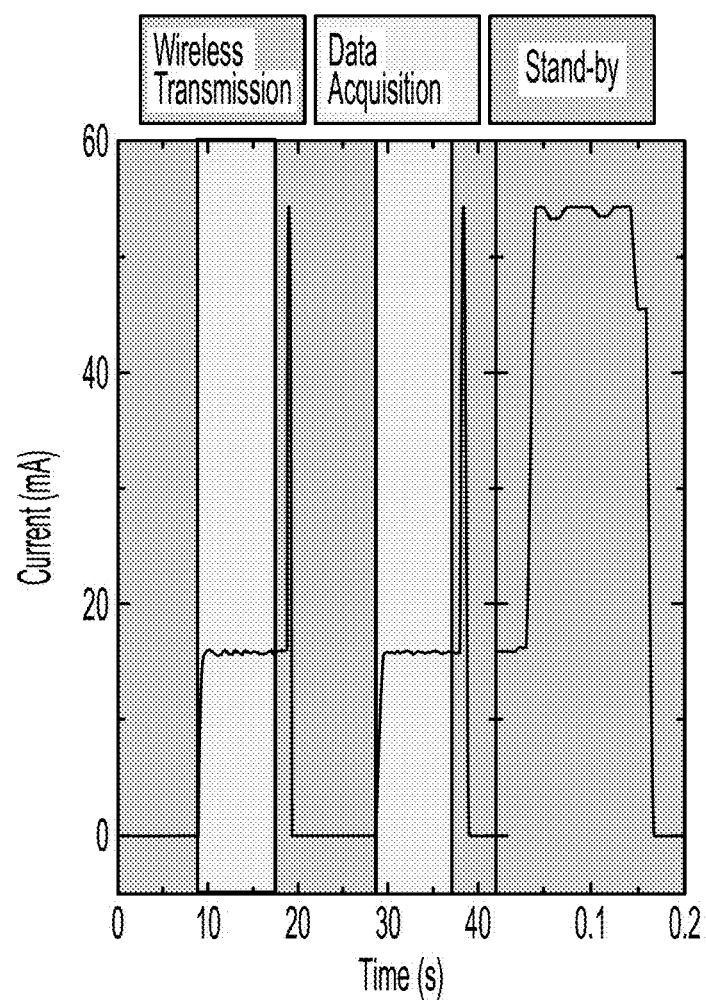
FIG. 2C provides (left panel) power consumption for the electronics (operated at 5 V) undergoing phases of stand-by, data-acquisition and wireless signal-transmission and (right panel) power consumption for the signal transmission phase at smaller time scale.

The system combined by the electronics and the sensing array with eight gFETs demonstrates high power efficiency. For the MCU programmed to repeat the measurement 10 seconds after finishing of the previous data-acquisition and-transmission circle, power consumption was 16 mA during data-acquisition and ~10 μA in stand-by mode, as shown in FIG. 2c. Note that the power consumption for signal transduction by the gFETs was negligible (<1 nW), an advantage of using nanomaterial-based FETs. When the wireless transceiver was operated at its highest level (20 dBm) which allows broadcasting with a range of 500 meters, the power consumption of the system was 54 mA with negligible transmission period (<0.2 s), resulting in negligible energy consumption as well. The break-down of the power budget for the system is shown elsewhere herein at Table 1, where the component estimates agree well with our measurements.

Given the $10^2$-$10^3$ mAh capacity of commercial low-cost batteries, our system could automatically operate for 280 days using a button cell battery (240 mAh) or 870 days with a AAA lithium battery (750 mAh), assuming 20 cycles of data acquisition and wireless data transmission per day.

Figure 3A:
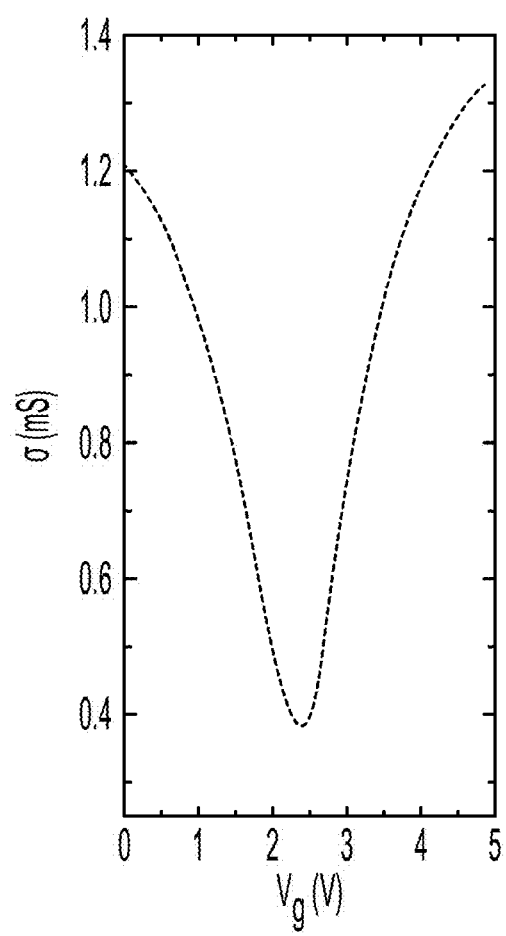
FIG. 3A provides $\sigma$-$V_g$ characteristic for a gFET functionalized with BPA-specific aptamer in tap water.

An exemplary electrical experiment was performed by calibrating the concentration-response curve. First measured were σ-$V_g$ characteristics for a BPA aptasensor based on gFETs functionalized with BPA-specific aptamer in tap water (FIG. 3a). The measured curve demonstrates the characteristic V-shape for gFETs, with carrier mobility in the range ~2500 cm$^2$ V$^{-1}$ s$^{-1}$, indicating outstanding electrical transport properties of the graphene we prepared.

Figure 3B:
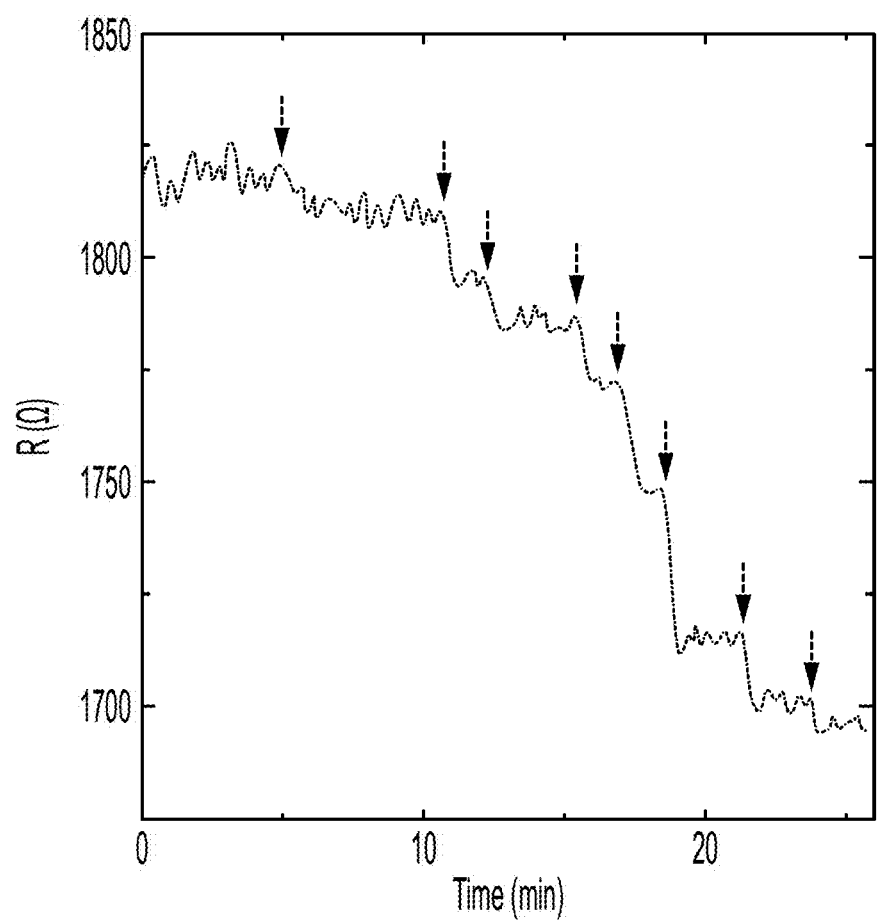
FIG. 3B provides resistance of a BPA aptasensor responding to tap water spiked with BPA with different concentrations.

The resistance of graphene channels in the array was measured to quantify toxic analytes spiked in tap water. For detection against BPA, the back-gate voltage was fixed at 1.75 V with maximized transconductance. As shown in FIG. 3b, c, as BPA concentration varies from 0.2 ng/ml to 0.04 mg/mL, the resistance changes by ~8%, well falling in the linear optimized regime in the σ-$V_g$ characteristics (FIG. 3a). The reduction of the graphene channel resistance well agrees with the negative charge polarity of BPA (pKa ~9.6), which upon adsorption by the aptamer can increase the charge neutral point of the graphene. Due to the low noise characteristic of the gFET-based aptasensors and the efficient filtering circuit of the ECB, the BPA concentration was well resolved with signal-to-noise ~7. The detection limit of of the BPA aptasensor, 0.1 ng/mL, is well below the guidelines of the Minnesota Department of Health, 20 ng/mL. The dissociation constant derived from the data is 16.7±0.9 ng/mL, in good agreement with values based on more conventional measurements, 2.0 ng/Ml.

Figure 3C:
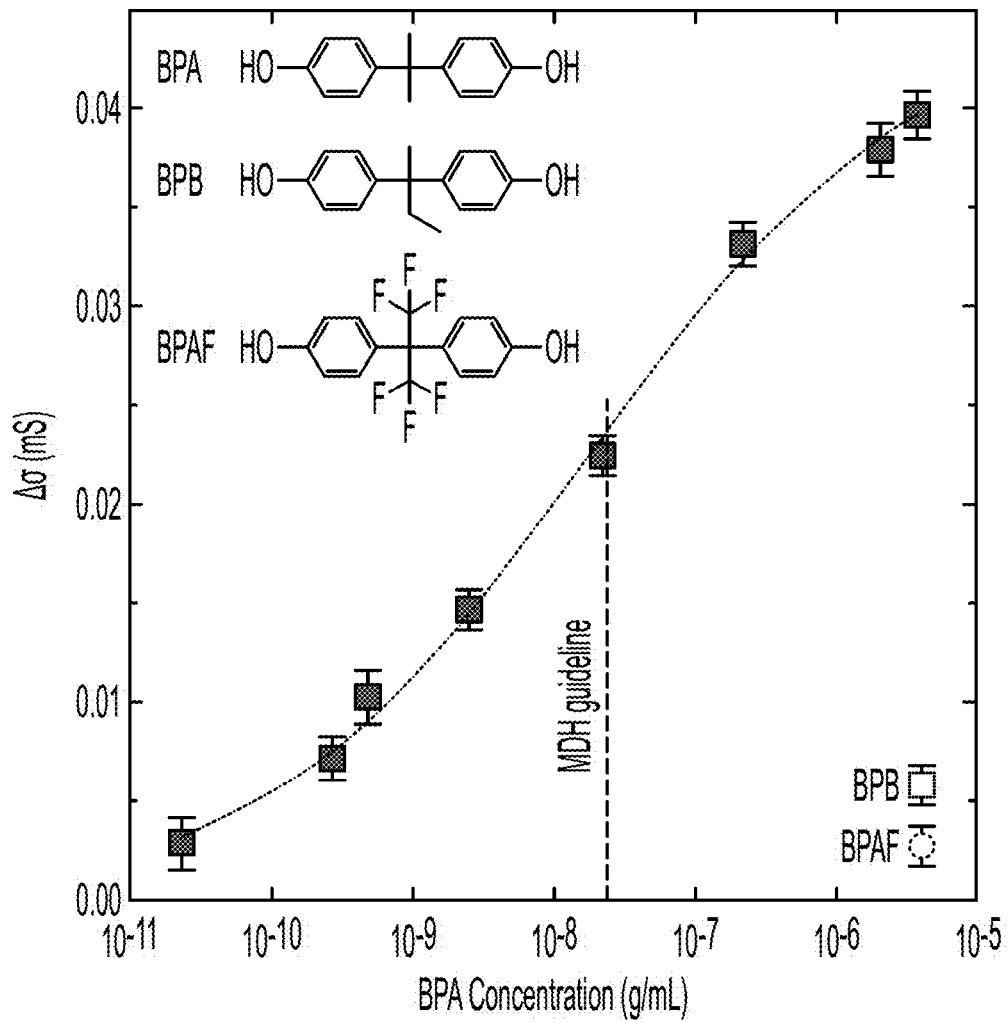
FIG. 3C provides the response of the BPA aptasensor to BPA concentration and the negative controls BPB and BPAF with the data for BPA fit by Hill-Langmuir equation FIG. 3D provides reversibility testing of resistance of BPA aptasensor.
Figure 3D:
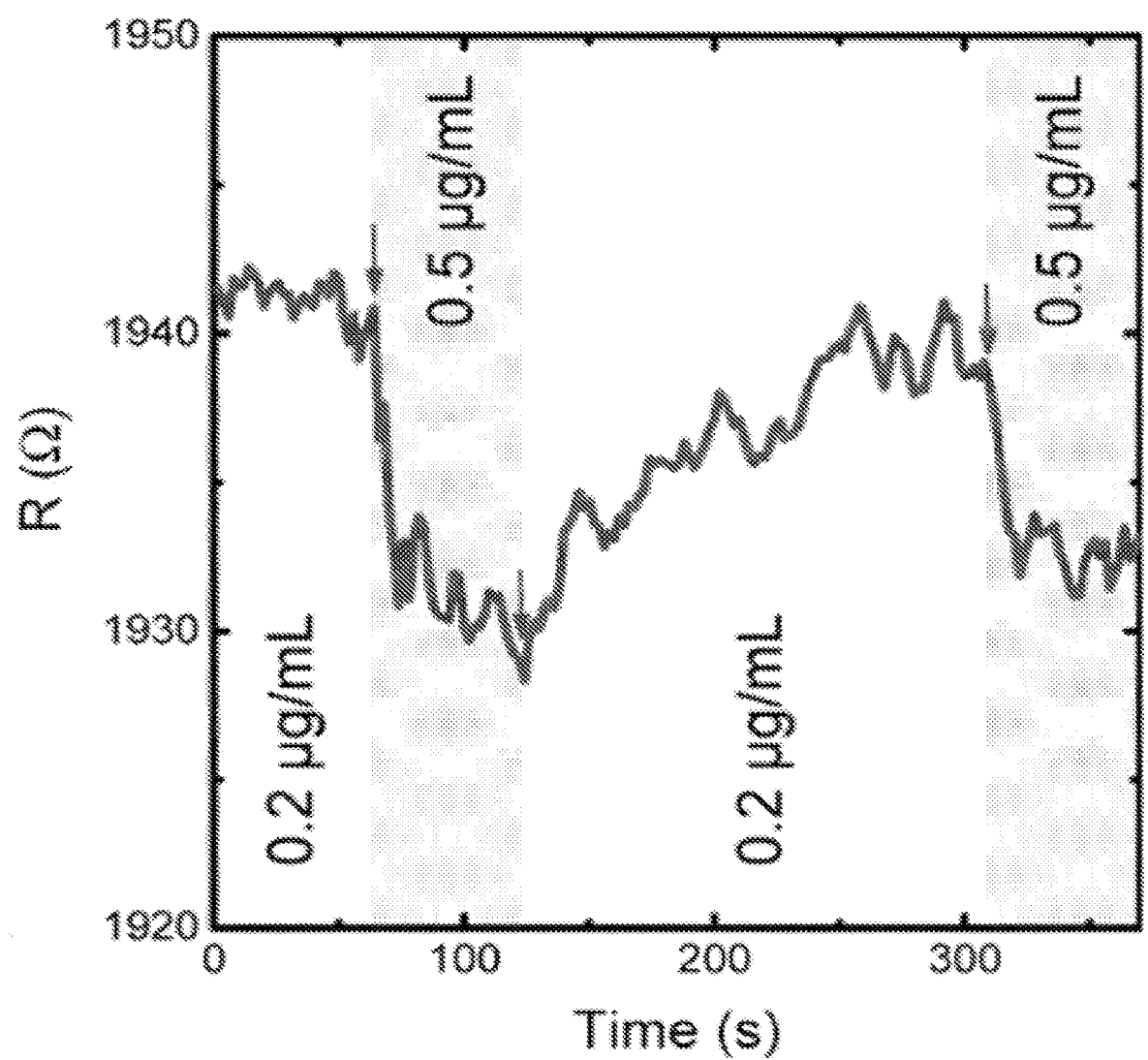
FIG. 3E provides the response of the mercury aptasensor to Hg(II) (solid squares) and the control Cu(II) (open squares), with the data for Hg(II) fit by Hill-Langmuir equation. The error bars are smaller than the data points.
Figure 3E:
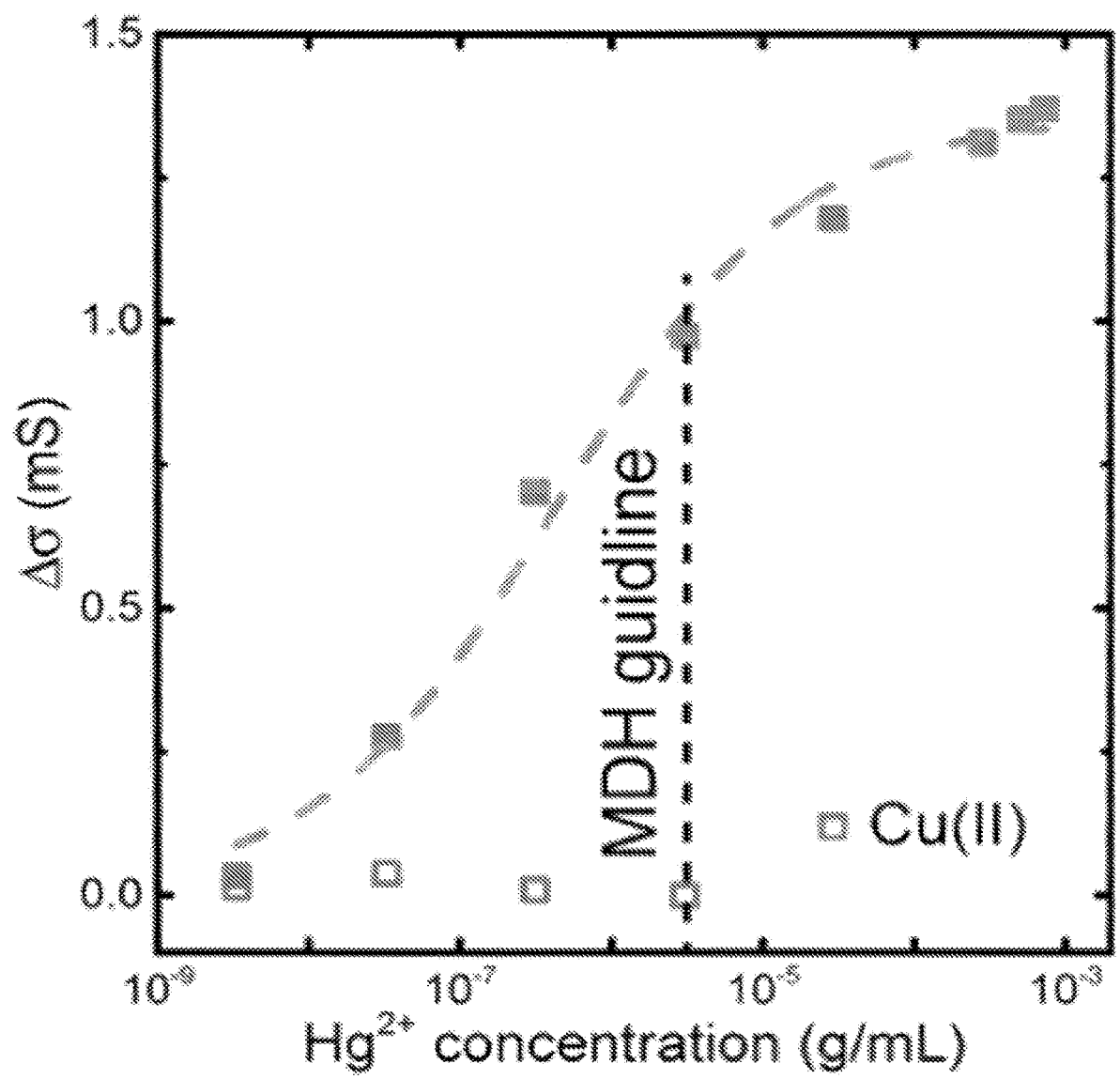

The BPA apatsensor also demonstrates high selectivity and reversibility. As shown, in, e.g., FIG. 3c, the responses of the sensor to two bisphenol chemicals, bisphenol B (BPB) and bisphenol AF (BPAF) with extremely similar chemical formula with respect to BPA, were negligible at high concentration (2.2 μg/mL). As another control experiment, an array functionalized with control aptamer was used to test BPA (as described elsewhere herein). The response is negligible over a broad range of BPA concentration. The reversibility of the BPA aptasensors, tested by increasing/decreasing the concentration of BPA multiple times as shown in FIG. 3e, demonstrates minimal hysteresis effect as the concentration was varied: approximately 30% of the signal uncertainty. These observations show that the gFET aptasensors are functioning according to their design, with responses that reflect specific binding of the target to the aptamer even in the complex background of tap water.

Figure 6:
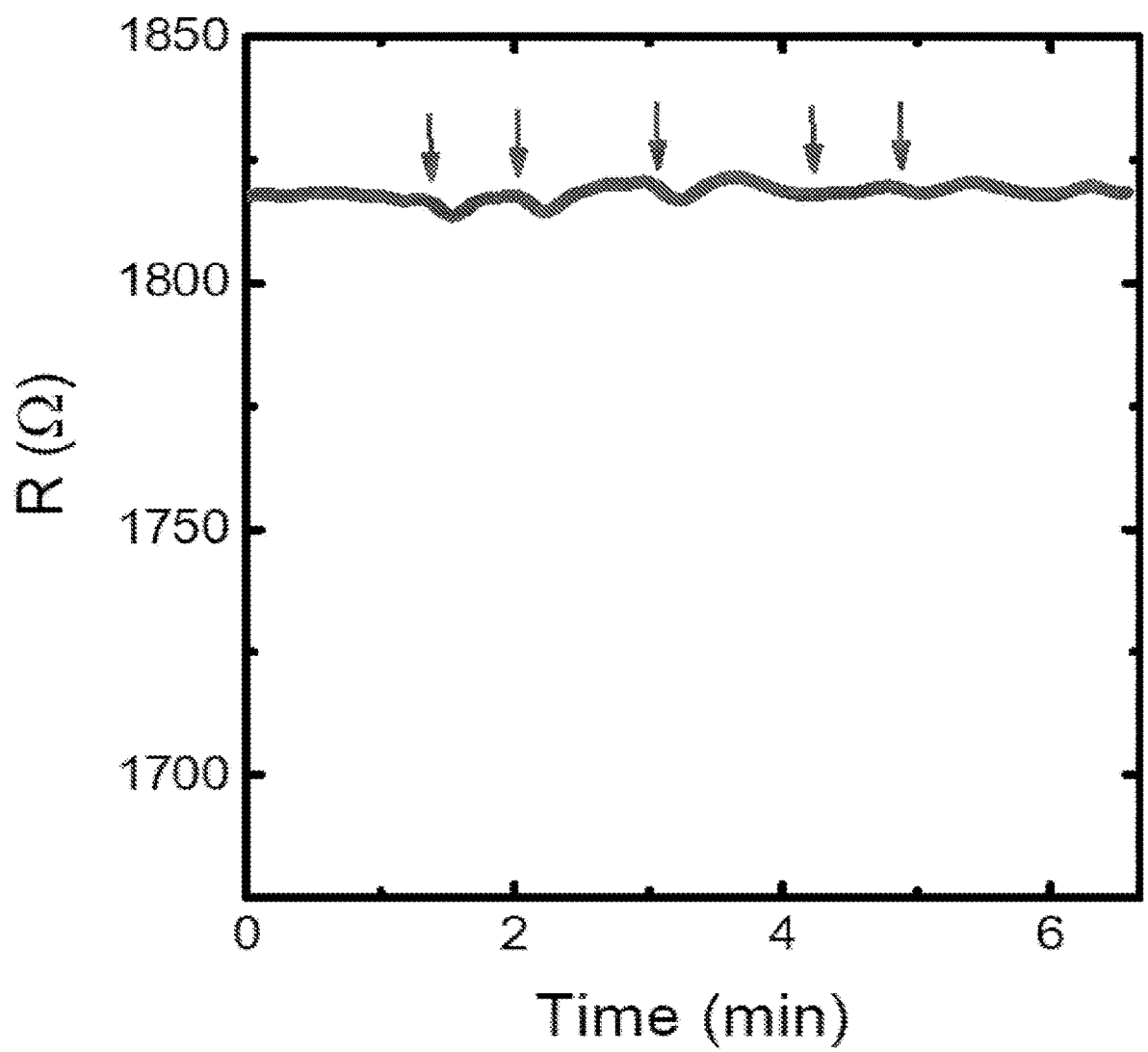
FIG. 6. Resistance of a control-aptamer functionalized graphene transistor to application of BPA-spiked tap water with different final concentration.

Also tested was HgCl$_2$-spiked water using a gFET array functionalized with an aptamer that binds specifically to Hg(II). With high mobility (3800 cm$^2$ V$^{-1}$ s$^{-1}$), the gFET was tuned with optimized point for the back-gate voltage at 0. (See FIG. 6.)

High sensitivity and selectivity was observed with this device (FIG. 3f). The detection limit, 2 ng/mL, was approximately three order of magnitude smaller than the guidelines of the Minnesota Department of Health for these targets, 2 μg/mL Hg(II). In the whole range of tested Hg(II) concentration between the lowest and the highest detection limits, the resistance changed by ~65%. For graphene-based heavy-metal-ion sensors, such a trend has been reported, which can be attributed to either the doping or the structure-switching effect. The dissociation constant derived from the data, 0.44±0.13 μg/mL, is in good agreement with values based on more conventional measurements, 0.46 μg/mL. The minor discrepancy between the data and the fitting by Hill- Langmuir equation can be understood by the fact that the range covered by the conductance variation caused by the change of Hg(II) concentration, ~1.4 mS exceeds the perfectly linear regime of the $\sigma$-$V_g$ characteristics (~0.4 mS).

For multiplexed testing, an gFET array was functionalized with the two different types of aptamers against BPA and Hg(II) respectively at two different regions (FIG. 1a). Transistors at each region were back-gated with specific voltage fixed at their own optimized points. After the chip was loaded onto the electronics, tap water spiked with either BPA or Hg(II) was applied alternatively to the array and the responses were recorded.

Figure 4A:
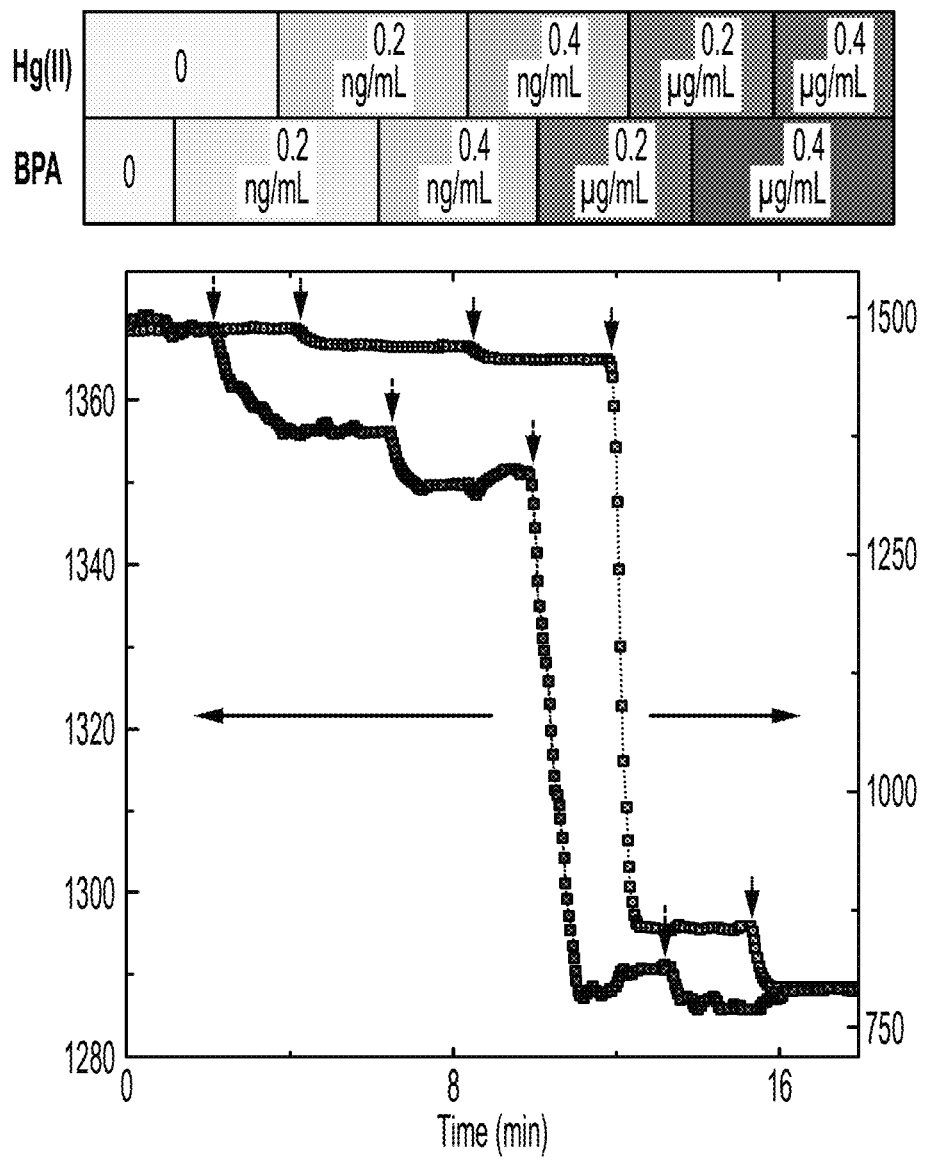
FIG. 4A provides resistance of two transistors in a multiplexed BPA/Hg(II) aptasensor responding to application/addition of tap water samples spiked with either BPA (lower line) or Hg(II) (upper line, further to right-hand side of figure). The final concentration for the solution was labeled on top of the plot.

As shown in FIG. 4a, the sensors on the same chip demonstrates excellent multiplexity as both BPA and Hg(II) coexist in the tap water on the sensing array. The gFETs functionalized with BPA-specific aptamer changed considerably when BPA was added while the addition of Hg(II) resulted in minimal reduction to the response which can be understood by the enhancement of Debye screening caused by the additive mercury ions; on the other hand, the Hg(II)-specific apatmer functionalized gFETs only responded noticeably to the addition of Hg(II).

Figure 4B:
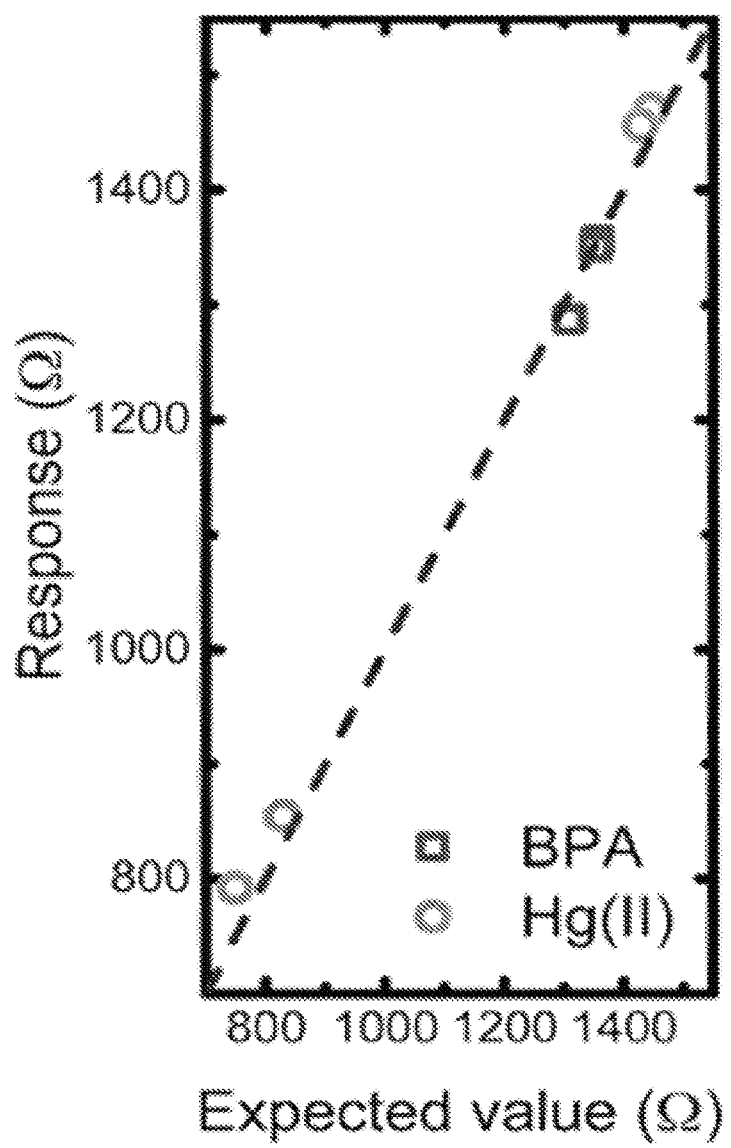
FIG. 4B provides a comparison of the measured responses (x-axis) to their expected values (y-axis) based on Hill-Langmuir equation with parameters obtained from FIG. 3. The dash line representing x=y is for eye-guiding. The error bars are smaller than the data points.
Figure 5:
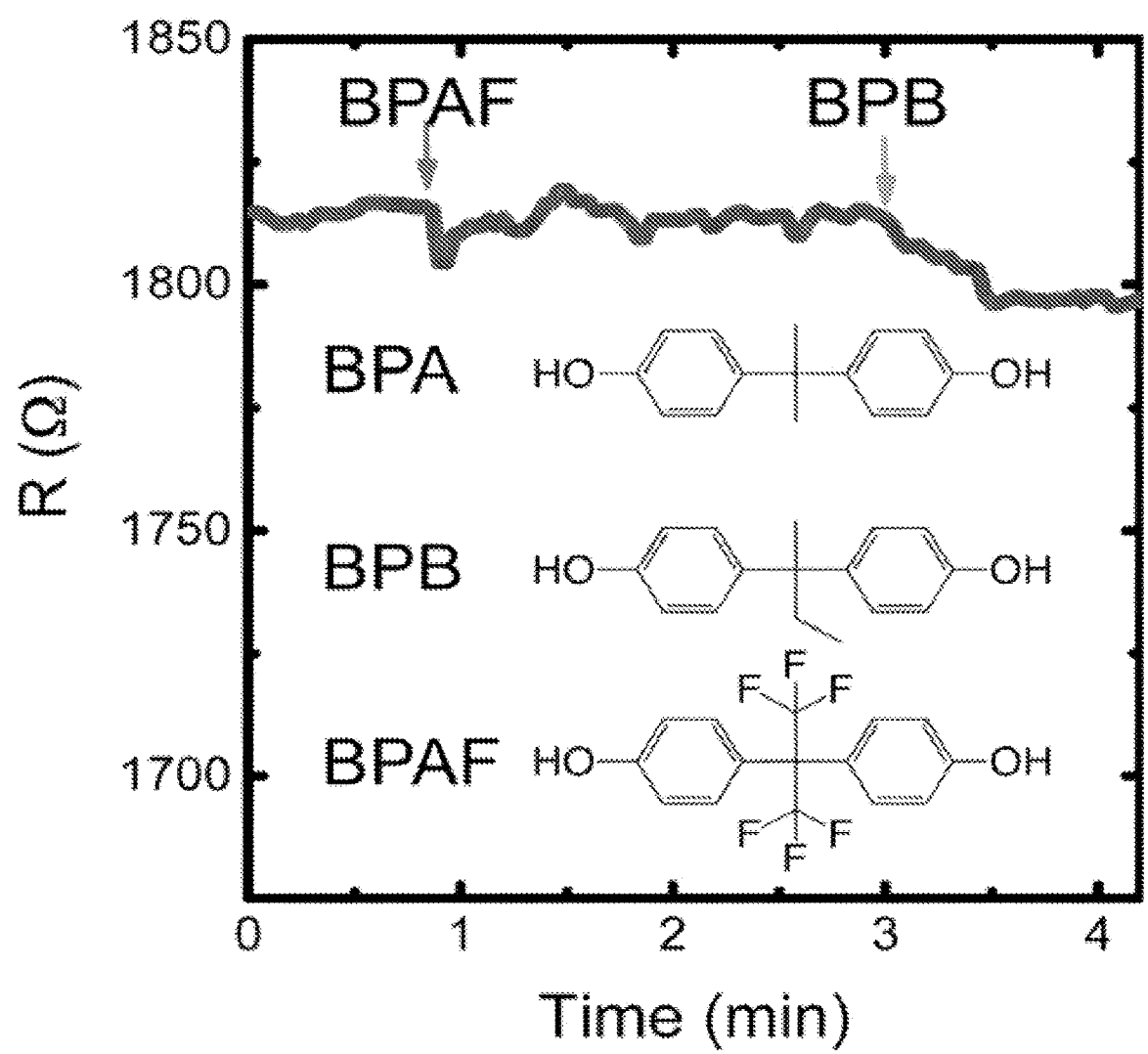
FIG. 5. The resistance of a BPA aptasensor in response to the addition of tap water spiked with BPB and BPF.

The measured response for both aptasensors was compared to the expected responses calculated from the calibration curves in FIGS. 2c and 2e. As shown in FIG. 4b, the BPA aptasensor response agrees well with the calculated value. For the Hg(II) aptasensor, the highest discrepancy between the measured value at 0.4 μg/mL was <5% higher than the response predicted by the Hill-Langmuir curve derived from FIG. 2e.

In summary, provided we developed a novel multiplexed graphene-aptasensor system capable of real-time quantification of the concentration of organic/inorganic toxins in tap water with high sensitivity and selectivity. An illustrative aptasensor was driven by a miniaturized robot allowing automatic data acquisition and wireless signal transmission with high signal-to-noise ratio and power efficiency. By utilizing a wireless data transmission function of the system, a large amount of testing can be performed with simultaneous data collection. By means of modern data analysis and mining tools such as machine learning, the implementation of the system leads to considerable progress in building scientific understanding of environmental toxicology.

CVD Growth of Large-Area Graphene

Monolayer graphene was grown via low pressure chemical vapor deposition on a copper foil substrate (99.8%, 25 μm thick, Alfa Aesar) in a four-inch quartz tube furnace. The copper was annealed for 60 minutes at 1020° C. in ultra-high purity hydrogen (99.999%; flow rate 80 sccm). Graphene was then synthesized using methane as a precursor (temperature 1020° C.; hydrogen flow rate 80 sccm; methane flow rate 10 sccm; pressure 850 mT; growth time 20 min). The tube was then cooled to room temperature in 40 minutes.

Graphene Transfer

A sacrificial layer of 500-nm thick poly (methyl methacrylate) (PMMA) was spin-coated on top of the graphene/copper substrate. The sample was baked for 2 minutes at 100° C., then connected to the cathode of a power supply and immersed in a 50 mM sodium hydroxide solution in DI water. A current ~1.5 A was applied between the cathode and a platinum anode in the electrolyte solution. Hydrogen bubbles were generated between graphene and the copper foil, causing the PMMA/graphene film to detach from the copper substrate. The PMMA/graphene film was then washed in a series of DI-water baths and transferred onto the surface of a fused silica substrate on which Cr/Au electrodes and a $HfO_2$ dielectric layer had previously been fabricated. The sample was left to dry for one hour, then baked at 150° C. for 2 minutes before the PMMA film was removed by washing with acetone and isopropyl alcohol. The sample was then dried with compressed nitrogen.

Device Fabrication

Fused silica wafer was heated to 400° C. to promote adhesion. Polymethylglutarimide (MicroChem), or PMGI, was spin-coated onto the wafer at 4000 rpm for 45 s, followed by softbake at 180° C. for 5 min. Then photoresist S1813 (MICROPOSIT) was coated at 5000 rpm for 45 s and followed by softbake at 100° C. for 2 min. The wafer was exposed by UV light with dose of 140 mJ/cm$^2$ and developed by MF-319 developer (MicroChem). Then a 5 nm Cr layer and a 45 nm Au layer were evaporated onto the sample at the speed of 0.2 nm/s and 1 nm/s respectively. A lift-off process was then performed in remover 1165 (MICROPOSIT).

A layer of 1 nm Al was evaporated onto the sample at the speed of 0.5 A/s. The sample taken out of the evaporator was left in air for thorough oxidization. Then ALD was used to grow 50 nm $HfO_2$ onto the $Al_2O_3$ sticking layer of the sample. For the ALD process, the precursors were $Hf[N(CH_3)_2]_4$ (HFDMA) and $H_2O$; the growth temperature was 150° C.

To expose gold leads below $HfO_2$ dielectric layer for contacting graphene channels and wire bonding, photoresist AZ 5214E (Merck Performance Materials) was used in an image reversal mode. At first AZ 5214E was spin-coated on the wafer at the speed of 4000 rpm for 45 s, followed by softbake at 100° C. for 1 min. Then the wafer was exposed to UV light with dose of 108 mJ/cm$^2$, followed by softbake at 100° C. for 45 s. A flood exposure of 1500 mJ/cm$^2$ was carried out to complete the image reversal process. Certain areas of $HfO_2$ were exposed by developing with AZ 422 developer (Merck Performance Materials), following by Ar (20 sccm) and $CHF_3$ (40 sccm) plasma etching of the exposed $HfO_2$ for 8 min at 30 mTorr with power of 200 V. After etching, the remained resist was removed by AZ 400T remover (Merck Performance Materials) and hydrochloride acid was used to washed away residues behind plasma etching.

Another layer of gold contacts was further deposited at the areas exposed in the $HfO_2$ dielectric layer. The mask-fabrication process was exactly the same as for defining the first layer of gold leads. A layer of 65 nm Au was evaporated onto the sample at the speed of 1 nm/s. Then a protection layer of S1813 was coated at 5000 rpm for 45 s before the wafer was diced into 0.8×0.8 mm pieces of arrays. Then arrays were liftoff in 1165 to remove photoresist and gold.

Graphene was transferred to each single array using bubbling transfer method (see graphene growth and transfer description elsewhere herein) and then baked at 150° C. for 3 min. Then the array was rinsed by acetone and IPA to remove the PMMA coated in transfer process.

To define graphene channels, PMGI was spin-coated onto the array at 4000 rpm for 45 s and followed by softbake at 125° C. for 5 min. Then S1813 was coated at 5000 rpm for 45 s and followed by softbake at 100° C. for 2 min. The array was exposed to UV light with dose of 80 mJ/cm$^2$ and developed by MF-319 for ~45 s. The exposed graphene was etched by O₂ plasma (etch power 60 KW) under the pressure of 0.8 torr for 20 s. Then 1165 was used to strip photoresist before acetone and IPA were used to rinse the array. The array was then annealed in tube furnace under flowing hydrogen (250 sccm) and argon (1000 sccm) at 250° C. for 1 hour.

Functionalization Of Graphene with Aptamer Molecules

The array was soaked in 1 mM PBS solution in DMF for 20 h, and then rinsed by three DMF bath, following by one IPA and DI water successively to wash off residues.

Aminated aptamer in phosphate buffer solution was heated to 95° C. for 10 min and then cooled down to room temperature gradually in 30 min. The array was incubated in the DNA solution for 3 h, rinsed by DI water thoroughly, soaked in 10 mM ethanolamine solution for 30 min which blocks the NHS groups of the unreacted PBASE, and then rinsed in DI water thoroughly.

Exemplary Aptamer Sequences

The following aptamer sequences are illustrative only and do not serve to limit the scope of the present disclosure or the appended claims.

```
BPA-aptamer
CCGGTGGGTGGTCAGGTGGGATAGCGTTCCGCGTATGGCCCAGCGCATCA

CGGGTTCGCACCA

BPA-control-aptamer
CGCAGCGCGCCCCTGAGTACTGTCCGCCCAACGGTGTGACGGCCCTGCGA

TCAACGATTG

Hg(II)-aptamer
TCCAAGCTCTTTTCTGCAGCTATTCTTGTTTCGAAACTTGCTAAGCTGCG

T
```

Exemplary Power-Consumption Break-Down

The break-down of the power consumption for the miniaturized electronics (operated at 5V) driving a gFET-based array is shown in Table 1 below:

TABLE 1

Break-down of the power budget for the handheld electronics.
All components except the DUT were operated at 5 V.

|  | Standby | On |
| --- | --- | --- |
| CMU | 6.2 µA | 6.75 µA (1 MHz) |
| ADC | <1.5 µA | ~350 µA |
| DAC | <1 µA | 2.7 mA |
| RF Transceiver | 0.1 µA | ~50 mA (20 dBm) |
| DUT | 0 | <1 nW |
| Estimated | ~9 µA | >10 mA |
| Measured | 11.1 µA | ~16 mA |

Exemplary Control Testing for a BPA Aptasensor

Tap water spiked with BPA with different final concentration (2.2 ng/mL, 22 ng/mL, 0.22 µg/mL, 2.2 µg/mL, and 4.4 µg/mL) was tested on a graphene field-effect transistor functionalized by control aptamer (sequence). The result is shown in FIG. S1.

Testing of Hg(II) Aptasensor

Figure 7A:
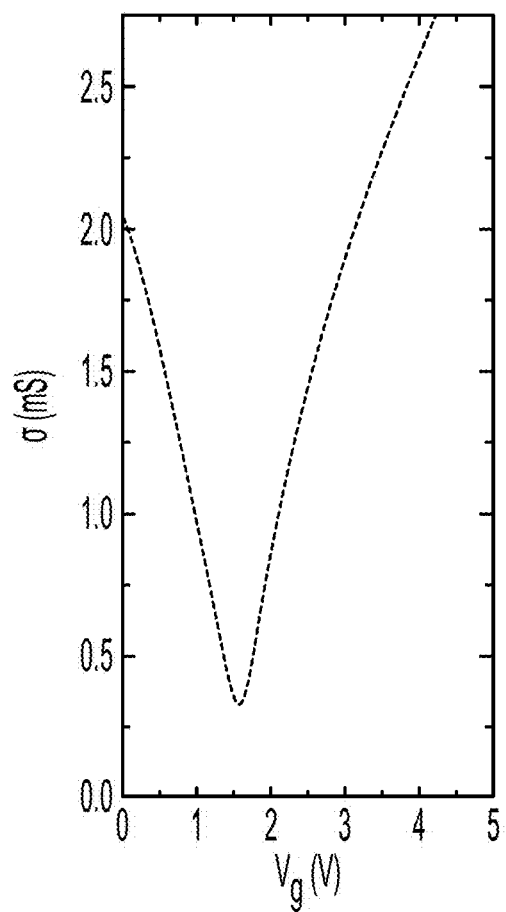
FIG. 7A provides a $\sigma$-$V_g$ relationship for a gFET functionalized with Hg(II)-specific aptamer in tap water.
Figure 7B:
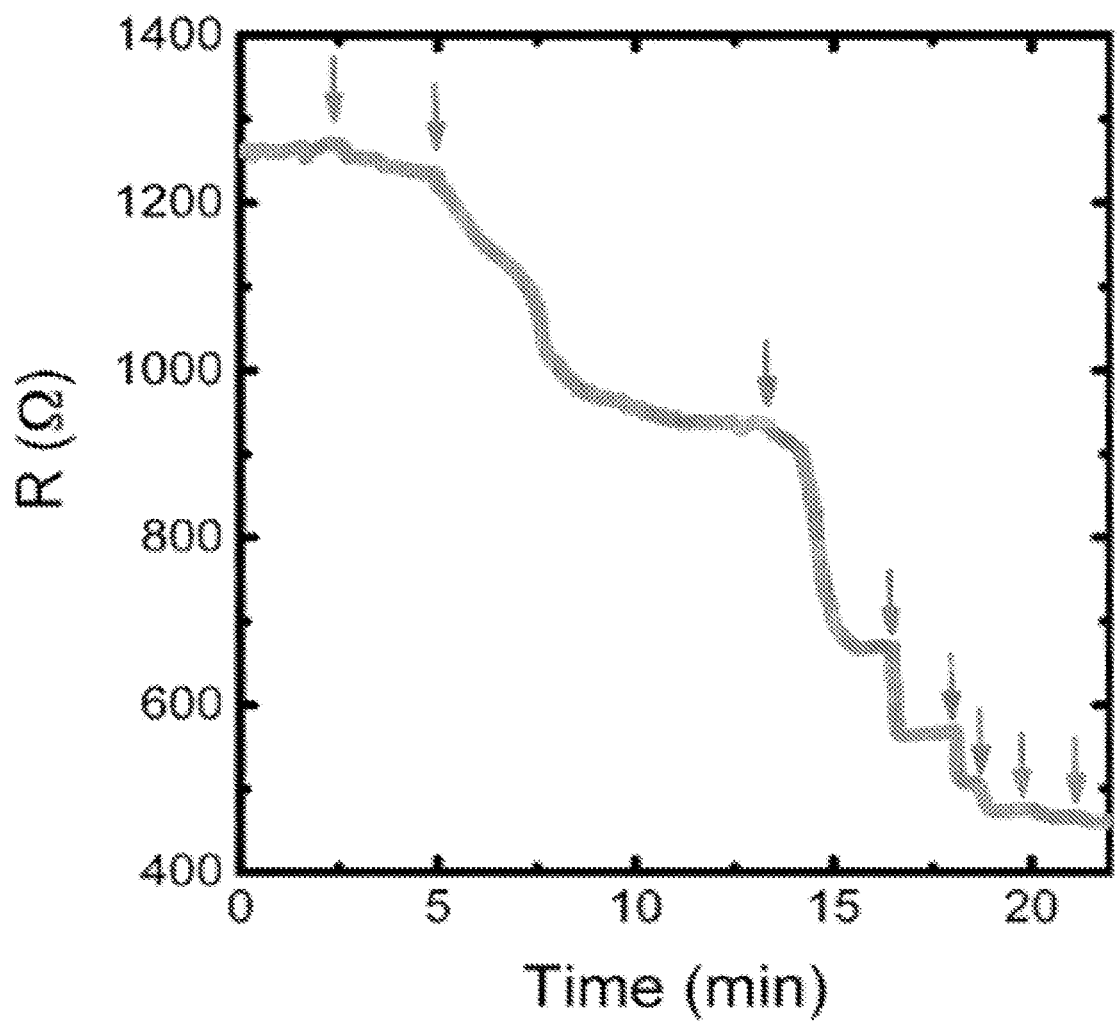
FIG. 7B provides resistance of a Hg(II) gFET aptasensor responding to tap water spiked with Hg(II) with different concentrations.
Figure 7C:
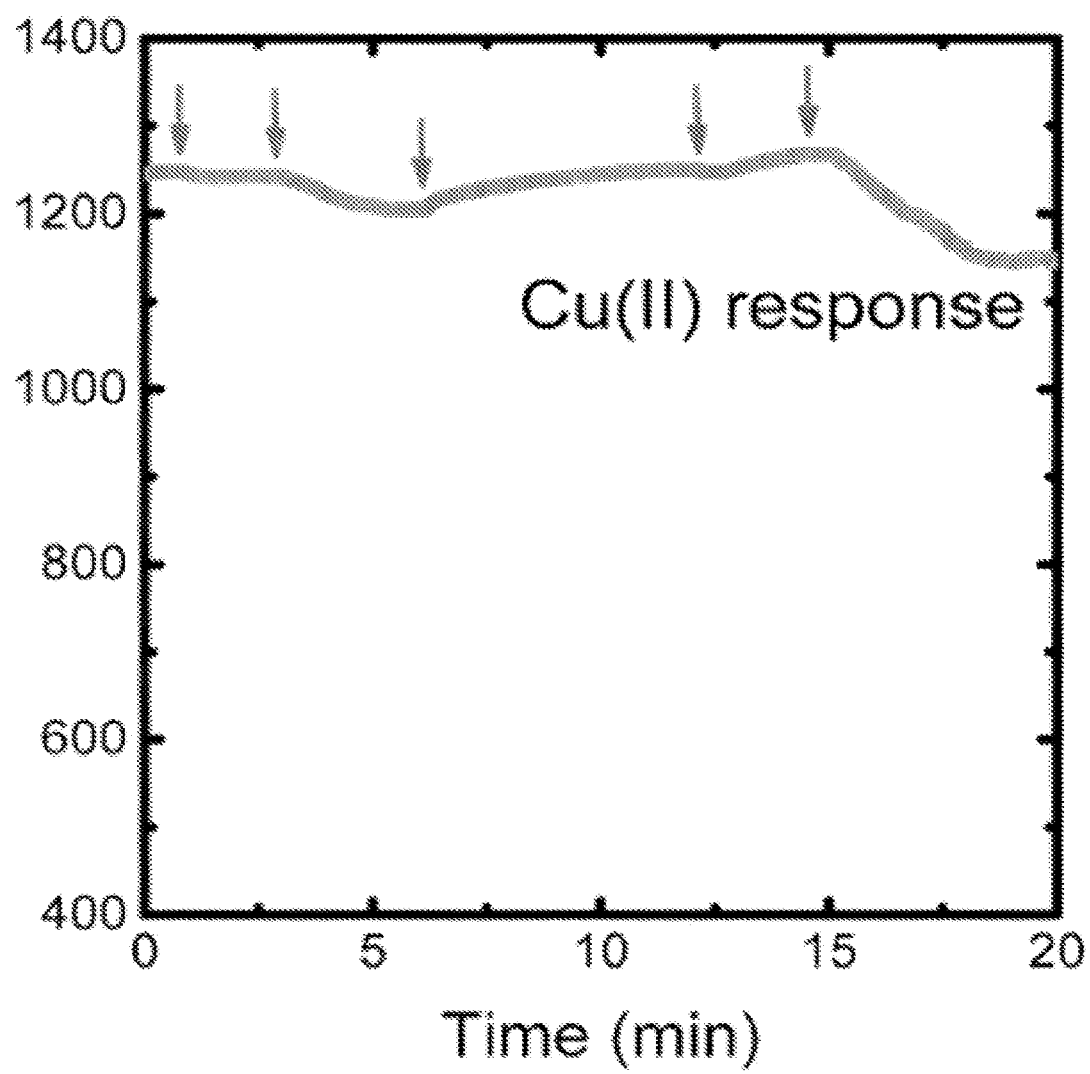
FIG. 7C provides the resistance of a Hg(II) aptasensor responding to tap water spiked with the negative control (arrows) heavy metal, Cu(II), at various concentrations.

Testing results are shown in FIG. 7. As shown, FIG. 7a provides a $\sigma$-$V_g$ relationship for a gFET functionalized with Hg(II)-specific aptamer in tap water, FIG. 7b provides resistance of a Hg(II) gFET aptasensor responding to tap water spiked with Hg(II) with different concentrations, and FIG. 7c The resistance of Hg(II) aptasensor responding to tap water spiked with the negative control (arrows) heavy metal, Cu(II), at various concentrations.

EXEMPLARY EMBODIMENTS

The following embodiments are exemplary only and do not serve to limit the scope of the present disclosure or the appended claims Embodiment 1. A sensor device, comprising: a portion of graphene and/or graphene oxide; and an aptamer in electrical communication with the portion of graphene and/or graphene oxide.

The portion of graphene and/or graphene oxide can include either or both of graphene or graphene oxide. The portion of graphene and/or graphene oxide can consist of or consist essentially of either graphene or graphene oxide.

The portion of graphene can be single- or multi-layer graphene. The portion of graphene can even comprise single- and multi-layer regions.

Embodiment 2. The sensor device of Embodiment 1, wherein the portion of graphene and/or graphene oxide is in electronic communication with a source electrode, a drain electrode, a gate electrode, or any combination thereof. An electrode can be metallic, but can also be of a carbonaceous material.

Embodiment 3. The sensor device of any one of Embodiments 1-2, wherein the aptamer is directly attached to the portion of graphene and/or graphene oxide or wherein the aptamer is attached to the portion of graphene and/or graphene oxide via one or more linkers.

As one example, the aptamer can be directly connected to the portion of graphene and/or graphene oxide by a chemical bond, an orbital interaction, and the like. The apatmer can also be connected to the portion of graphene and/or graphene oxide via a linker or linkers, such as a hydrocarbon chain, an aromatic molecule, and the like. Other suitable linkers include, e.g., 1-Pyrenebutyric acid N-hyroxysuccinimide ester (PBASE) as mentioned in the paper. 4-carboxy benzenediazonium tetrafluoroborate and similar compounds can also be used.

Embodiment 4. The sensor device of Embodiment 3, wherein the aptamer is attached to the portion of graphene and/or graphene oxide or attached to the one or more linkers, if present, via pi-pi orbital interaction, via covalent bonding, via ionic bonding, via hydrogen bonding, or any combination thereof.

Embodiment 5. The sensor device of any one of Embodiments 1-4, further comprising a controller unit that comprises one or more of a voltage regulator, a digital-to-analog converter, and an analog-to-digital converter.

Embodiment 6. The sensor device of Embodiment 5, wherein the controller unit is configured to modulate a gate voltage of the sensor device.

Without being bound to any particular theory, back-gate voltage can be modulated/set to achieve optimal performance in the device. This can be done in an automated way. The disclosed device configuration allows local-gating for each single sensor device in the array in its optimized carrier density. At their optimized carrier density, all devices are in maximal sensitivity, as well as analytical range with change of response proportional to the change of carrier density. Using this strategy, one can analyze multiple target biomolecules at the same time, with high sensitivity.

Embodiment 7. The sensor device of any one of Embodiments 1-6, further comprising a transceiver.

Embodiment 8. The sensor device of Embodiment 6, wherein the transceiver is a wireless, radio frequency (RF) transceiver.

Embodiment 9. The sensor device of any one of Embodiments 4-7, wherein the controller is configured to apply less than about 0.1 V to the portion of graphene and/or graphene oxide. The power consumption for a single sensor device can be less than about 1 uW.

Embodiment 10. The sensor device of any one of Embodiments 1-9, wherein the aptamer comprises a nucleic acid aptamer or a peptide aptamer.

Embodiment 11. The sensor device of any one of Embodiments 1-10, wherein the aptamer is configured to interact (e.g., bind) preferentially to a metal or metal ion. In some embodiments, the aptamer can be one that binds preferentially to mercury. An aptamer can be one that binds preferentially to metal ions such as, e.g., copper, cadmium, chromium, arsenic, and lead.

Embodiment 12. The sensor device of any one of Embodiments 1-11, wherein the aptamer is configured to interact (e.g., bind) preferentially to an aromatic compound. Some such suitable compounds include, e.g., bisphenol A (BPA), bisphenol B, toluene, para-xylene, trimethylbenzene, nitrobenzene, p-nitrophenol, p-nitrobenzaldehyde, atrazine, tetracycline, estradol and 2,4-dinitrochlorobenzene, and the like.

Embodiment 13. The sensor device of any one of Embodiments 1-12, wherein the portion of graphene and/or graphene oxide is disposed on a substrate. The substrate can comprise one or more materials, and can also be formed of a homogenous material. The substrate can also be formed of a layered material.

Embodiment 14. The sensor device of Embodiment 13, wherein the substrate comprises silicon, silicon oxide, or any combination thereof.

Embodiment 15. The sensor device of any one of Embodiments 1-14, wherein the sensor device comprises any of (a) a plurality of aptamers in electronic communication with the portion of graphene and/or graphene oxide, or (b) a plurality of units each comprising an aptamer in electronic communication with a portion of graphene and/or graphene oxide, or any combination of (a) and (b).

An aptamer can be individually addressable (e.g, electronically individually addressable). A unit can also be individually electronically addressable. For example a device can include first and second aptamers, which which aptamers signals can be separately monitored.

In some embodiments, a device can comprise an array of aptamers. A device can comprise an array of aptamers, with each aptamer being in electronic communication with a separate portion of graphene and/or graphene oxide, e.g., a tiled array of graphene and/or graphene oxide portions.

A given graphene and/or graphene oxide portion can be individually addressable and can be in electronic isolation from other graphene and/or graphene oxide portions. A device can include duplicative elements, e.g., 10 aptamer-graphene and/or graphene oxide units having aptamers that preferentially interact with BPA, 10 aptamer-graphene and/or graphene oxide units having aptamers that preferentially interact with benzene, and so on.

A unit can comprise, e.g., a separate or individual portion of graphene and/or graphene oxide. As an example, a device can include a first unit that comprises one or more graphene and/or graphene oxide portions that in turn are in electronic communication with a first aptamer that is configured to bind preferentially to a first analyte. The device can also include a second unit that comprises one or more graphene and/or graphene oxide portions that in turn are in electronic communication with a second aptamer that is configured to bind preferentially to a second analyte. In this way, a device can be constructed in a modular fashion in which a user can assemble various units to detect the various analytes of interest.

A device can include duplicative units so as to ensure quality control of sampling and/or to ensure that the device will detect a certain analyte even if some portion of the device is damaged. For example, a device may include multiple copies of the same aptamer.

Embodiment 16. A method, comprising: contacting a sensor device according to any one of Embodiments 1-15 with a sample; and measuring an electrical signal of the sensor device related to an interaction between the aptamer and the sample.

As an example, a user can measure a change in signal related to an interaction between BPA in a sample and an aptamer of the device that preferentially interacts with BPA.

Embodiment 17. The method of Embodiment 16, wherein the electrical signal comprises a current, a voltage, a resistance, or any combination thereof.

Embodiment 18. The method of any one of Embodiments 16-17, wherein the sample comprises a target molecule. Suitable target molecules are described elsewhere herein and include, e.g., metals, aromatic compounds, and the like. A target molecule can comprise, e.g., a small molecule, a protein, a nucleic acid, a cell, a tissue, or even an organism.

Embodiment 19. The method of Embodiment 18, wherein the target molecule is present in the sample at less than about 20 ng/mL.

Embodiment 20. The method of any one of Embodiments 16-19, wherein the target molecule comprises a metal, an aromatic compound, a small molecule, a protein, a nucleic acid, a cell, a metal, an aromatic compound, or both.

Embodiment 21. A method, comprising: contacting a sample to an aptamer in electronic communication with a portion of graphene and/or graphene oxide; and measuring an electrical signal of the sensor device related to an interaction between the aptamer and the sample.

Embodiment 22. A method of fabricating a detector device, comprising: placing an aptamer into electrical communication with the portion of graphene and/or graphene oxide; and placing the portion of graphene and/or graphene oxide into electrical communication with at least one electrode.

Embodiment 23. The method of Embodiment 22, further comprising disposing the portion of graphene and/or graphene oxide on a substrate.

Embodiment 24. The method of any one of Embodiments 22-23, wherein the aptamer is placed into electrical communication with the portion of graphene and/or graphene oxide by being directly attached to the portion of graphene and/or graphene oxide or by being connected to the portion of graphene and/or graphene oxide by one or more linkers.

Embodiment 25. The method of Embodiment 22, wherein the attaching is effected by pi-pi orbital interaction, by covalent bonding, by ionic bonding, by hydrogen bonding, or any combination thereof.

Embodiment 26. The method of any one of Embodiments 22-25, wherein the attaching is effected by a displacement reaction.

REFERENCES

The following documents are incorporated herein by reference in their entireties for any and all purposes.

1. Stuart JD, Capulong CP, Launer KD, & Pan X (2005) Analyses of phenolic endocrine disrupting chemicals in marine samples by both gas and liquid chromatography-mass spectrometry. Journal of Chromatography A 1079:136-145.
2. Ballesteros-Gomez A, Rubio S, & Perez-Bendito D (2009) Analytical methods for the determination of bisphenol A in food. Journal of Chromatography A 1216:449-469.
3. Fukata H, Miyagawa H, Yamazaki N, & Mori C (2006) Comparison of Elisa- and LC-MS-based methodologies for the exposure assessment of bisphenol A. Toxicology Mechanisms and Methods 16:427-430.
4. Gumpu MB, Sethuraman S, Krishnan UM, & Rayappan JBB (2015) A review on detection of heavy metal ions in water—An electrochemical approach. Sensors and Actuators B: Chemical 213:515-533.
5. Huang Y-L, Hsiung T-M, Chen Y-Y, Huang Y-F, & Huang C-C (2010) Colorimetric detection of heavy metal ions using label-free gold nanoparticles and alkanethiols. The Journal of Physical Chemistry C 114(39):16329-16334.
6. Vishnubhotla R, et al. (2017) Scalable graphene aptasensors for drug quantification. AIP Advances.
7. Wiedman GR, et al. (2017) An aptamer-based biosensor for the azole class of antifungal drugs. mSphere 2(4): e00274-00217.
8. Ping J, Xi J, Saven J, Liu R, & Johnson ATC (2017) Quantifying the effect of ionic screening with protein-decorated graphene transistors. Biosensors and Bioelectronics 89:689-692.
9. Balandin AA (2013) Low-frequency 1/f noise in graphene devices. Nature Nanotechnology 8:549-555.
10. Keefe AD, Pai S, & Ellington A (2010) Aptamers as therapeutics. Nature Reviews 9:537-550.
11. Ping J, Vishnubhotla R, Vrudhula A, & Johnson ATC (2016) Scalable production of high sensitivity, label-free DNA biosensors based on back-gated graphene field effect transistors. ACS Nano 10(9):8700.
12. Anonymous (2014) Bisphenol A in Drinking Water; http://www.health.state.mn.us/divs/eh/risk/guidance/gw/bpainfosheet.pdf. (Minnesota Department of Health).
13. Anonymous (2014) Environmental Protection Agency Safe Drinking Water Act Standards: Microbiological, Radiological, and Inorganic Contaminants; http://www.health.state.mn.us/divs/eh/water/factsheet/com/ioc.html. (Minnesota Department of Health).
14. Jo M, et al. (2011) Development of single-stranded DNA aptamers for specific bisphenol A detection. Oligonucleotides 21:85-91.
15. Qu H, et al. (2016) Rapid and label-free strategy to siolate aptamers for metal ions. ACS Nano 10:7558-7565.
16. Weiss JN (1997) The Hill equation revisited: uses and misuses. FASEB J. 11(11):835-841.
17. Chen J-H, et al. (2008) Charge-impurity scattering in graphene. Nature Physics 4:377-381.
18. Lerner MB, et al. (2017) Large scale commercial fabrication of high quality graphene-based assays for biomolecule detection. Sensors and Actuators B: Chemical 239:1261-1267.
19. An JH, Park SJ, Kwon OS, Bae J, & Jang J (2013) High-performance flexible graphene aptasensor for mercury detection in mussels. ACS Nano 7 (12): 10563-10571.
20. Li Y, et al. (2016) Fully integrated graphene electronic biosensor for label-free detection of lead (II) ion based on G-quadruplex structure-switching. Biosensors and Bioelectronics 89:758-763.

What is claimed:

1. A sensor device, comprising:
a portion of graphene and/or graphene oxide in electronic communication with a gold source electrode, a drain electrode, a gate electrode, or any combination thereof, and
an aptamer in electrical communication with the portion of graphene and/or graphene oxide,
the portion of graphene and/or graphene oxide connected to said aptamer via at least one linker that comprises 4-carboxybenzenediazonium tetrafluoroborate.

2. The sensor device of claim 1 wherein the portion of graphene and/or graphene oxide is disposed on a substrate.

3. The sensor device of claim 2 wherein the substrate comprises silicon, silicon oxide, or any combination thereof.

* * * * *

UNITED STATES PATENT AND TRADEMARK OFFICE
CERTIFICATE OF CORRECTION

PATENT NO. : 12,405,260 B2
APPLICATION NO. : 18/504369
DATED : September 2, 2025
INVENTOR(S) : Alan T. Johnson, Jr. et al.

It is certified that error appears in the above-identified patent and that said Letters Patent is hereby corrected as shown below:

On the Title Page

In Other Publications,

Under Column no. 2, Page 2, Line no. 4, Replace:
"lons"
With:
--Ions--

Under Column no. 2, Page 2, Line no. 29, Replace:
"lons","
With:
--Ions",--

In the Specification

Under Column no. 5, Line no. 51, Replace:
"KHz."
With:
--kHz.--

Under Column no. 10, Line nos. 50-51, Replace:
"4-carboxy benzenediazonium"
With:
--4-carboxybenzenediazonium--

In the Claims

Under Column no. 15, Claim 1, Line no. 5, Replace:
"thereof,"

Signed and Sealed this
Twenty-eighth Day of October, 2025

John A. Squires
*Director of the United States Patent and Trademark Office*

With:
--thereof;--